United States Patent [19]

Benigni et al.

[11] Patent Number: 5,175,303
[45] Date of Patent: Dec. 29, 1992

[54] PREPARATION OF 7-(DIPHENYLMETHYL)OXY-9A-METHOXYMITOSANE

[75] Inventors: Daniel A. Benigni, Elbridge; Kenton L. Shultis, Manlius, both of N.Y.; Henry S. L. Wong, Durham, Conn.

[73] Assignee: Bristol-Myers Squibb Company, New York, N.Y.

[21] Appl. No.: 766,299

[22] Filed: Sep. 27, 1991

Related U.S. Application Data

[62] Division of Ser. No. 491,380, Mar. 8, 1990, Pat. No. 5,075,454.

[51] Int. Cl.$^5$ .......................................... C07D 487/04
[52] U.S. Cl. .................................................. 548/422
[58] Field of Search ....................................... 548/422

[56] References Cited

U.S. PATENT DOCUMENTS

| | | | |
|---|---|---|---|
| 3,306,821 | 2/1967 | Schroeder | 424/119 |
| 4,059,573 | 11/1977 | Robinson | 530/344 |
| 4,691,023 | 9/1987 | Vyas et al. | 548/422 |
| 4,691,024 | 9/1987 | Shirahata et al. | 548/422 |
| 4,803,212 | 2/1989 | Vyas et al. | 514/338 |
| 4,814,445 | 3/1989 | Vyas et al. | 544/111 |
| 4,866,180 | 9/1989 | Vyas et al. | 546/271 |

FOREIGN PATENT DOCUMENTS

| | | |
|---|---|---|
| 0074245 | 3/1983 | European Pat. Off. . |
| 0116208 | 8/1984 | European Pat. Off. . |
| 0324109 | 7/1989 | European Pat. Off. . |
| WO8607260 | 12/1986 | PCT Int'l Appl. . |
| 2164038 | 3/1986 | United Kingdom . |

OTHER PUBLICATIONS

Aboderin, A. A., et al., J. Am. Chem. Soc. 87, 5469–5472 (1965).
Adamson, R. J., et al. J. Chem. Soc. Perkin I. 2030–2033 (1975).
Bywood, R., et al., J. Chem. Soc. Perkin I, 2019–2021 (1975).
Cheng, L., et al., Journal of Medicinal Chemistry, vol. 20, No. 6, 767–770 (1977).
Iyengar, B. S. et al., J. Med. Chem., vol. 24, 975–981 (1981).
Matsui, M., The Journal of Antibiotics vol. XXI, No. 3, 189–198 (1968).
Sami, S. M., et al., J. Med. Chem. vol. 30, 168–173 (1987).
Stelakatos, G. C., et al., J. Chem. Soc (C) 1191–1199 (1966).
Taylor-Papadimitriou, J., et al., J. Chem. Soc. (C), 1830–1836 (1967).
Urakawa, C., et al., The Journal of Antibiotics, vol. XXXIII, No. 9, 804–809 (1980).
Vyas, D. M., et al., J. Org. Chem., vol. 51, No. 22, 4307–4309 (1986).
Vyas, D.M., et al., The Journal of Antibiotics, vol. 42, No. 7, 1199–1202 (1989).
Black T. H., Aldrichimica Acta, vol. 16, No. 1, 1983.
Elks, J. (ed), Recent Advances in the Chemistry of β-Lactam, Antibiotics, Special Pub. No. 28, The Chemical Society, 139–144 (1977).
Fieser & Fieser, Reagents for Organic Synthesis, vol. 1, p. 191 (1967).
Fieser & Fieser, Reagents for Organic Synthesis, vol. 1, pp. 338–339 (1967).
The Merck Index, 11th Edition, p. 473 (1989).
Sami, S. M., et al., J. Med Chem. 32, 703–708 (1989).
Patai, S. (ed), The Chemistry of Diazonium and Diazo Groups Part 1, John Wiley & Sons, 1978 pp. 261–264.

Primary Examiner—Joseph P. Brust
Assistant Examiner—Mary Susan H. Gabilan

[57] ABSTRACT

7-(Diphenylmethyl)oxy-9a-methoxymitosane is a novel intermediate for conversion into 7-amino and 7-oxy-9a-methoxymitosanes and is also useful for inhibiting mammalian tumor growth. The compound is prepared by reacting 7-hydroxy-9a-methoxymitosane with diazodiphenylmethane. In a preferred reaction, the compound is prepared from mitomycin C via 7-hydroxy-9a-methoxymitosane without drying (water removal). The intermediate is advantageously converted to the very effective anti-tumor agent 7-[2-(4-nitrophenyldithio)ethylamino]-9a-methoxymitosane in unexpectedly high yields using a two step process where the first step constitutes conversion to 7-[2-(2-pyridyldithio)ethylamino]-9a-methoxymitosane. or 7-[2-(3-nitro-2-pyridyldithio)ethylamino]-9a-methoxymitosane.

8 Claims, No Drawings

PREPARATION OF 7-(DIPHENYLMETHYL)OXY-9A-METHOXYMITOSANE

This is a divisional of copending application Ser. No. 07/491,380 filed Mar. 8, 1990, now U.S. Pat. No. 5,075,459.

TECHNICAL FIELD

This invention is directed to a novel mitosane which is useful as an intermediate, for example, in producing mitomycin C derivatives in which the 7-amino group bears an organic substituent incorporating a disulfide group and which also is useful for inhibiting mammalian tumor growth.

This invention is further directed at methods of making the novel mitosane.

This invention is also directed at a method of converting said novel mitosane to 7-[2-(4-nitrophenyldithio)ethylamino]-9a-methoxymitosane.

BACKGROUND OF THE INVENTION

Mitomycin C is the principal mitomycin produced by fermentation and is the commercially available form.

A useful semisynthetic approach to forming 7-substituted amino-9a-methoxymitosanes has centered on converting mitomycin C to the final product via mitomycin A as an intermediate where mitomycin C is converted to mitomycin A by hydrolyzing to form the corresponding 7-hydroxymitosane and methylating that compound with diazomethane as described, for example, in Vyas et al U.S. Pat. No. 4,691,023 or with 3-methyl-1-p-tolyltriazene as described, for example in Vyas, D.M., et al, J. Org. Chem. 1986, 51, 4307–4309. The procedure utilizing diazomethane has the disadvantage that this reactant is very hazardous to handle and therefore undesirable for routine and large scale synthesis. The triazene route has the disadvantages of producing by-product toluidine which can react with mitomycin A product and which requires removal and of requiring the absence of water since the triazene reactant is unstable in the presence of water.

It is an object herein to provide a novel compound which is an intermediate for production of 7-substituted amino, 7-amino and 7-substituted oxy-9a-methoxymitosanes which is synthesized utilizing a much safer reactant than diazomethane and without the formation of by-product and which is readily prepared in the presence of water, and which also is useful as an antitumor agent.

It is a further object herein to provide methods of making such compound.

It is a further object herein to provide a method of converting said compound to 7-[2-(4-nitrophenylditho)ethyl-amino]-9a-methoxymitosane.

SUMMARY OF THE INVENTION

The novel compound provided herein is 7-(diphenylmethyl)oxy-9a-methoxymitosane.

The preparation of this compound according to one embodiment herein proceeds via the known compound 7-hydroxy-9a-methoxymitosane which is readily synthesized from mitomycin C and from mitomycin A. This preparation comprises the step of reacting 7-hydroxy-9a-methoxymitosane with diazodiphenylmethane to produce said novel compound.

When this preparation starts with mitomycin C, it can entail utilizing either aqueous mitomycin C containing fermentation derived solution or mitomycin C as a solid. The mitomycin C, whether in solution or solid form, is treated with aqueous hydroxide solution to produce an aqueous solution of basic 7-salt oxide-9a-methoxymitosane. Sodium hydroxide is the preferred hydroxide and reaction with it produces 7-Na$^+$O$^-$-9a-methoxymitosane. The resulting aqueous salt oxide solution can be either dried to produce a substantially water free residue which is reacted with acid, or is reacted with acid without first drying, thereby to produce 7-hydroxy-9a-methoxymitosane.

We first turn to the process where drying, i.e., water removal, is carried out. Freeze drying is preferred, and the lyophilized product (7-Na$^+$O$^-$-9a-methoxymitosane where aqueous sodium hydroxide was used as the aqueous hydroxide solution) is suspended utilizing a moderately polar solvent (e.g., acetone) for treatment with acid. The acid can be either in the form of a cation exchange resin or an acid solution and is used in sufficient amount to convert the 7-salt oxide group to 7-hydroxy. Use of a strong acid cation exchange resin in the hydrogen form is preferred. When cation exchange resin is used, after reaction is carried out, the resin is separated and the solvent is evaporated if it is incompatible with diazodiphenylmethane. The 7-hydroxy-9a-methoxymitosane is reacted with diazodiphenylmethane in a solvent or solvent combination in which these both are soluble (e.g., methylene chloride) to form the 7-(diphenylmethyl)oxy-9a-methoxymitosane product; reaction can be carried out, for example, at 0° C. to 30° C., for 1 to 10 hours using an excess of diazodiphenylmethane, e.g., 2 to 5 equivalents of diazodiphenylmethane. Purification is readily carried out by chromatography, e.g., on Al$_2$O$_3$ or SiO$_2$. Less pure material can be obtained without column chromatography by concentrating, removing excess diazodiphenylmethane by partitioning with a non polar solvent, followed by evaporation. Yields from mitomycin C of over 60% are typically obtained. This is unexpected in view of Sami, S.M., et al, J. Med. Chem. 1987, 30, 168–173 which indicates (page 169) that the procedure of reacting "solutions of 7-hydroxymitosane with appropriate diazoalkanes . . . was not useful for larger diazoalkanes" and which in Table 1 at page 170 (compound No. 7) shows a yield of 10% where benzyldiazomethane was reacted with "7-hydroxymitosane".

We turn now to the case where drying (i.e., water removal) is not carried out, i.e., in the case where aqueous solution of basic 7-salt oxide-9a-methoxymitosane is treated directly with acid. The acid is preferably aqueous phosphoric acid and is admixed to provide a pH of 4.7 to 6.5, very preferably from 5 to 6, to produce aqueous solution of 7-hydroxy-9a-methoxymitosane. The reaction of this with diazodiphenylmethane proceeds as follows. The diazodiphenylmethane is admixed. The solvent in which the diazodiphenylmethane is dissolved and/or which is otherwise admixed is a solvent or solvent combination in which both the 7-hydroxy-9a-methoxymitosane and diazodiphenylmethane are soluble and preferably is the combination of methylene chloride and methanol in a volume ratio of methylene chloride to methanol ranging, for example, from 0.5:1 to 3:1. The reaction between 7-hydroxy-9a-methoxymitosane proceeds despite the presence of water apparently as an extractive alkylation where the organic solvent extracts the 7-hydroxy-9a-methoxymitosane from the water phase for reaction in organic solvent phase (preferably methylene chloride). The alkylation reaction to produce 7-(diphenylmethyl)oxy-9a-methoxymitosane proceeds, for example, at a temperature ranging from 0° C. to 30° C. for 1 to 10 hours using an excess of diazodiphenylmethane, e.g., 2 to 5 equivalents of diazodiphenylmethane. During the alkylation reaction, acid, preferably aqueous phosphoric acid, is preferably added periodically as may be necessary to maintain the pH in the range of 4.7 to 6.5, very preferably 5 to 6. When the alkylation reaction is completed, organic phase is separated and substantially pure 7-(diphenylmethyl)oxy-9a-methoxymitosane is recovered, e.g., by drying to remove water and evaporating to remove organic solvent and recovering product from the residue by chromatography on $Al_2O_3$ or $SiO_2$. Additional product can be obtained by vigorously mixing the aqueous phase with diazodiphenylmethane in solvent for it and 7-hydroxy-9a-methoxymitosane, preferably methylene chloride, and reacting, preferably at 15° C. to 25° C. for 10 to 20 hours, and recovering additional product, e.g., by chromatography. Yields from mitomycin C, including product obtained from workup of the aqueous phase, of 40 to 60% have been obtained. These yields are unexpected in view of the Sami, et al article referred to above.

The resulting purified 7-(diphenylmethyl)oxy-9a-methoxymitosane can be reacted with amines wherein the amino or substituted amino group from the amine displaces the 7-(diphenylmethyl)oxy group to produce the corresponding 7-amino or 7-substituted amino compounds which are known antitumor agents. In other words, 7-(diphenylmethyl)oxy-9a-methoxymitosane is reacted with RNH or $RNH_2$ to produce 7-RN- or 7-RNH-9a-methoxymitosanes respectively where R is aliphatic or cycloaliphatic or aromatic group, which is substituted or unsubstituted, or where R forms a heterocyclic group with N. For example, 7-(diphenylmethyl)oxy-9a-methoxymitosane is reacted with p-nitrophenyldithioethylamine, e.g., as the hydrochloride acid addition salt, in triethylamine/methanol at 0° C. to 30° C. to produce 7-[2-(4-nitrophenyldithio)ethylamino-9a-methoxymitosane which is taught as an antitumor agent in Vyas et al, U.S. Pat. No. 4,691,023.

The resulting purified 7-(diphenylmethyl)oxy-9a-methoxymitosane can also be reacted with basified alcohol whereby the organic moiety of the alcohol displaces 7-(diphenylmethyl). Thus where KOH/methanol is used, the product is mitomycin A.

Where 7-(diphenylmethyl)oxy group is being replaced with a substituted dithioethylamino group, it is preferred to proceed through 7-[2-(2-pyridyldithio)ethylamino]-9a-methoxymitosane or 7-[2-(3-nitro-2-pyridyldithio)ethylamino]-9a-methoxymitosane as an intermediate. Thus, in the case of producing 7-[2-(4-nitrophenyldithio)ethylamino]9a-methoxymitosane, the 7-(diphenylmethyl)oxy-9a-methoxymitosane is converted to 7-[2-(2-pyridyldithio)ethylamino]-9a-methoxymitosane or 7-[2-(3-nitro-2-pyridyldithio)ethylamino]-9a-methoxymitosane which in a second step is converted to the product by displacement of 2-thiopyridyl or 3-nitro-2-thiopyridyl with 4-nitrothiophenol. The first step is readily carried out by reacting 7-(diphenylmethyl)oxy-9a-methoxymitosane with 2-pyridyldithioethylamine or 2-(3-nitro-2-pyridyldithio)ethylamine, in methanol and reacting at a temperature ranging from 15° C. to 25° C. The 2-pyridyldithioethylamine or 2-(3-nitro-2-pyridyldithio)ethylamine reactants may be added as hydrochloride acid addition salt together with the triethylamine or other neutralizing agent to convert the acid addition salt to the free base for reaction. While the reaction of 7-diphenylmethyl)oxy-9a-methoxymitosane with 2-pyridyldithioethylamine or 2-(3-nitro-2-pyridyldithio)ethylamine is similar to reactions with these and mitomycin A to produce the same products, the yield in the case of producing 7-[2-(4-nitrophenyldithio)ethylamino]-9a-methoxymitosane is increased substantially more compared to the direct route than would be expected considering the decrease or lesser percentage increase obtained by proceeding through the same intermediate compared to the direct route for mitomycin A.

A trivial system of nomenclature which has found wide use in the mitomycin literature and which is used herein identifies the foregoing ring system including several of the characteristic substituents of the mitomycins as mitosane.

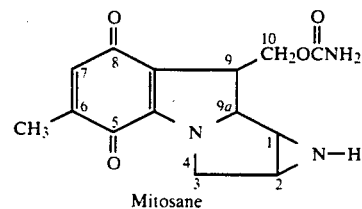
Mitosane

As to the stereochemical configuration of the products of this invention, it is intended when identifying them by the root name "mitosane" or by structural formula to identify the stereochemical configuration thereof as the same as that of mitomycin C.

DETAILED DESCRIPTION

The novel compound provided herein, i.e., 7-(diphenylmethyl)oxy-9a-methoxymitosane, has the formula

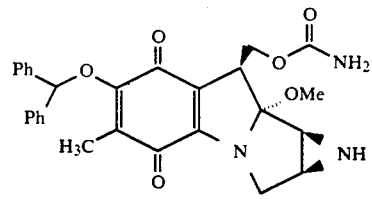

wherein "Ph" stands for phenyl. It is a dark red or maroon powder. It has a melting point of 96°–97° C. It is characterized by the following: $^1$H-NMR (pyr-d5) signals at δ. 1.85 (3H, s), 2.04 (1.H, t), 2.68 (1H, brs), 3.08 (1H,d), 3.11 (3H, s), 3.43 (1H,d), 3.96 (1H, dd), 4.08 (1H, d), 5.02 (1H, t), 5.43 (1H, dd), 7.19 to 7.38 (10H, m) and 7.42 (1H, s); UV λmax (methanol) 206, 325, 528 nm; IR KBr major bands 3427, 1730, 1632, 1578, 1450, 1404, and 1330 cm$^{-1}$.

We turn now to the method of making said compound which comprises reacting 7-hydroxy-a-methoxymitosane with diazodiphenyl-methane.

7-Hydroxy-9a-methoxymitosane has the formula

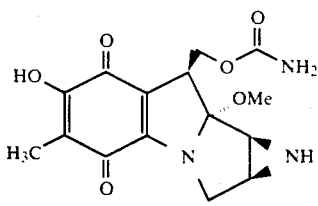

Preparations of this compound from mitomycin C and from mitomycin A are described in Matsui, M., et al, The Journal of Antibiotics, Vol. XXI, No. 3, 189–198 (Mar 1968).

Diazodiphenylmethane has the formula

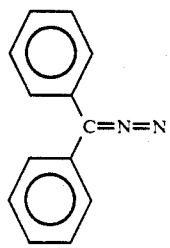

It can be prepared as described in Adamson, R.J., et al, J. Chem. Soc. Perkin I, 2030–2033 (1975).

These are reacted with or without water present in a solvent or solvent combination which does not adversely affect the reaction and in which both are soluble, at a reaction temperature of 0° C. to 30° C. for 1 to 10 hours using an excess of diazodiphenylmethane over 7-hydroxy-9a-methoxymethane, for example 2 to 5 equivalents of diazodiphenylmethane. Preferred solvents are methylene chloride, or methylene chloride and methanol in a volume ratio of methylene chloride to methanol ranging from 0.5:1 to 3:1. Other suitable solvents include, for example, ethyl acetate, isopropyl acetate, other esters, tetrahydrofuran, diethyl ether, other ethers, halogenated hydrocarbons such as chloroform and 1,2-dichloroethane, alcohols such as ethanol and propanols, and mixtures of these.

We turn now to the preferred processes herein for preparing said intermediate which comprise the step of reacting 7-hydroxy-9a-methoxymitosane with diazodiphenylmethane and which start with mitomycin C as a source of the 7-hydroxy-9a-methoxymitosane.

In these preferred processes, as previously indicated, the preferred first step is reacting mitomycin C in aqueous hydroxide solution to form aqueous solution of basic 7-salt-oxide-9a-methoxymitosane which is converted to 7-hydroxy-9a-methoxymitosane for reaction with diazodiphenylmethane. The preferred hydroxide solution is sodium hydroxide solution. Other suitable hydroxide solutions include, for example, aqueous potassium hydroxide solution, and aqueous lithium hydroxide solution. This first step is readily carried out utilizing the hydroxide in greater than stoichiometric amount (e.g., 1–1.5 equivalents) and reacting at 30° C. to 40° C. for 1½ to 4 hours. When sodium hydroxide is the hydroxide, the product is an aqueous solution of 7-sodium oxide-9a-methoxymitosane, i.e., 7-Na$^+$O$^-$-9a-methoxymitosane, which has the formula

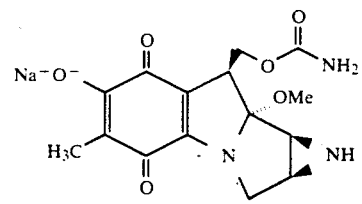

The aqueous solution can be dried for proceeding substantially in the absence of water or with only a minor amount of water present (e.g., less than a 10 mole ratio of H$_2$O:7-Na$^+$O$^-$-9a-methoxymitosane) to 7-(diphenylmethyl)oxy-9a-methoxymitosane (hereinafter the dry route) or can be processed to form 7-(diphenylmethyl)oxy-9a-methoxymitosane even through substantial water (e.g. a 0.1 molar aqueous solution of 7-Na$^+$O$^-$-9a-methoxymitosane) is present (hereinafter the wet route).

We turn firstly to the dry route. In the dry route, the basic aqueous salt oxide solution is dried to form essentially dry (less than a 10 mole ratio of H$_2$O:7-Na$^+$O$^-$-9a-methoxymitosane) solid 7-salt oxide-9a-methoxymitosane (when sodium hydroxide is the reactant the essentially dry solid product is 7-sodium oxide-9a-methoxymitosane). Drying is preferably by freeze drying although other drying methods, e.g., evaporation or spray drying may also be used. When freeze drying is used, an appropriate cycle comprises cooling to −50° to −80° C. and drying under a vacuum of approximately 0.1 mm Hg for 10–30 hours. As previously indicated, the essentially dry solid product is suspended in a moderately polar solvent. As previously indicated, acetone is the preferred moderately polar solvent. Other suitable solvents for suspension of dry product include, for example, other ketones, tetrahydrofuran, esters such as ethyl acetate, and halogenated hydrocarbons such as chloroform and 1,2-dichloroethane. As previously indicated the 7-salt oxide is reacted with acid either as a solution or as strong acid cation exchange resin in the hydrogen form to prepare the 7-hydroxy-9a-methoxymitosane reactant. Use of cation exchange resin is preferred since such can be used in the absence of water. Suitable acid solutions include, for example, aqueous phosphoric, sulfuric, hydrochloric, and other mineral acids. A sufficient amount of acid is utilized to protonate the salt oxide to 7-hydroxy-9a-methoxymitosane. The reaction with the acid is readily carried out at a temperature ranging from 0° C. to 30° C. for a time period ranging from 5 minutes or less up to about 3 hours or more. Where strong acid cation exchange resin is utilized, a reaction temperature of 20° to 25° C. and a reaction time of 1 to 2 hours is preferred. After the 7-hydroxy-9a-methoxymitosane product is formed, any cation exchange resin is separated, and as previously indicated solvent is removed if it is incompatible with the step of reacting 7-hydroxy-9a-methoxymitosane with diazodiphenylmethane. For the dry route, the step of reacting 7-hydroxy-9a-methoxymitosane with diazodiphenylmethylmethane is preferably carried out utilizing methylene chloride as the sole solvent and reaction is preferably carried out without heating or cooling for 3 to 5 hours.

We turn now to the wet route, that is where a substantial amount of water (e.g., a 0.1 molar aqueous solution of 7-Na$^+$O$^-$-9a-methoxymitosane) is present in proceeding to 7-(diphenylmethyl)oxy-9a-methoxymitosane. This is quite advantageous since mitomycin C can be obtained for use in this route without entirely purifying the mixture resulting from fermentation production of mitomycin C, e.g., fermentation derived solution can be used, thereby reducing or eliminating loss of mitomycin C that occurs on separation thereof from the fermentation broth and purification. This route allows other 7-oxo-9a-methoxymitosanes and 7-amino-9a-methoxymitosanes which may be present in the fermentation broth to be converted to 7-hydroxy-9a-methoxymitosane thereby increasing yields. Furthermore, drying in the production of 7-hydroxy-9a-methoxymitosane can be eliminated since aqueous 7-hydroxy-9a-methoxymitosane is reacting with diazodiphenylmethane. The reaction of diazodiphenylmethane with 7-hydroxy-9a-methoxymitosane in the presence of water to produce 7-(diphenylmethyl) oxy-9a-methoxymitosane in substantial yield constitutes an unobvious result since the art fails to teach reaction of diazomethanes with 7-hydroxy-9a-methoxymitosane in the presence of water.

Turning now to preferred conditions for the wet route, the aqueous solution of 7-salt oxide-9a-methoxymitosane (7-Na$^+$O$^-$-9a-methoxymitosane when aqueous sodium hydroxide is the hydroxide solution reacted with mitomycin C) is reacted directly with acid. While aqueous acid solutions or strong acid cation exchange resin in the hydrogen form can be used as the acidifying agent, in this case, unlike in the dry route, aqueous acid solution is preferred over cation exchange resin since use of cation exchange resin requires a resin separation step whereas the water introduced with aqueous acid does not need to be removed for reaction of diazodiphenylmethane with 7-hydroxy-9a-methoxymitosane. The reaction is readily carried out, for example, by combining diphenyldiazomethane solution with the 7-salt oxide-9a-methoxymitosane solution, adjusting the pH into the desired range of about 4 to 7 with acid solution, preferably 5-15% phosphoric acid, maintaining the pH in said desired range by the periodic addition of acid solution while maintaining the temperature in the range of 0° C. to 30° C. and adding additional diphenyldiazomethane solution if needed. As previously indicated methanol is preferably used in combination with methylene chloride reaction solvent. The methanol aids in extracting formed 7-hydroxy-9a-methoxymitosane from aqueous phase for reaction in the organic phase with diazodiphenylmethane.

We turn now to the reaction of 7-(diphenylmethyl)oxy-9a-methoxymitosane with primary or secondary amines wherein amino or substituted amino group from amine reactant displaces the 7-(diphenylmethyl)oxy group to produce the corresponding 7-amino or 7-substituted amino-9a-methoxymitosanes. Suitable primary and secondary amine reactants include, for example, those listed in Schroeder U.S. Pat. No. 3,306,821 at column 3, line 38 to column 4, line 6 and the list of these at column 3, line 38 to column 4, line 6 of Schroder U.S. Pat. No. 3,306,821 is incorporated herein by reference. The broad application of 7-(diphenylmethoxy)oxy-9a-methoxymitosane for reaction with primary and secondary amines is shown by specific examples hereinafter of reaction of it with p-anisidine, morpholine, and ethanolamine as well as dithioethylamines to produce aminodisulfides (such as those aminodisulfides disclosed in Vyas et al U.S. Pat. No. 4,691,023 and Shirahata et al U.S. Pat. No. 4,691,024). One very important reaction exemplified hereinafter is reaction of 7-(diphenylmethyl)oxy-9a-methoxymitosane with 2-(p-nitrophenyldithio)ethylamine, e.g., as the hydrogen chloride acid addition salt, to produce the very effective antitumor compound 7-[2-(4-nitrophenyldithio)ethylamino]-9a-methoxymitosane; the p-nitrophenyldithioethylamine reactant is readily prepared by starting with the known disulfide $H_3COOCSSCH_2CH_2NH_2.HCl$ and reacting with p-nitrothiophenol according to the procedure of Brois, S.F., et al, J. Am. Chem. Soc. 92, 7629–7631 (1970). Other important reactions of 7-(diphenylmethyl)oxy-9a-methoxymitosane with amines to produce very the stable intermediates 7-[2-(3-nitro-2-pyridyldithio)ethylamino-9a-methoxymitosane and 7-[2-(2-pyridyldithio)ethylamino]-9a-methoxymitosane, are described later. In general, reaction of 7-(diphenylmethyl)oxy-9a-methoxymitosane with primary or secondary amines to produce 7-amino and 7-substituted amino-9a-methoxymitosanes is readily carried out in methanol at a temperature ranging from 0° to 30° C. for 1 to 50 hours. When the amine is utilized as an acid addition salt, it is readily converted to the free base for reaction by addition to the reaction mixture of triethylamine or other suitable neutralizing agent.

We turn now to the reaction of 7-(diphenylmethyl)oxy-9a-methoxymitosane with basified alcohol whereby the organic moiety of the alcohol displaces 7-(diphenylmethyl). Suitable alcohols include, for example, methanol, ethanol, propanols, butanols, and other lower alcohols. Suitable basifying agents include, for example, KOH, NaOH, and LiOH. This reaction is readily carried out by reacting at 0° to 30° C. for 1 to 10 hours.

We turn now to the reaction herein to replace the 7-(diphenylmethyl)oxy group with substituted dithioethylamino group comprising first converting 7-(diphenylmethyl)oxy-9a-methoxymitosane to 7-[2-(2-pyridyldithio)ethylamino-9a-methoxymitosane or 7-[2-(3-nitro-2-pyridyldithio)ethylamino]-9a-methoxymitosane intermediate and then converting the intermediate to 7-substituted dithioethylamino-9a-methoxymitosane.

The process for conversion to 7-[2-(2-pyridyldithio)ethylamino-9a-methoxymitosane comprises reacting 7-(diphenylmethyl)oxy-9a-methoxymitosane with 2-pyridyldithioethylamine, e.g., as the hydrochloride salt. This reaction is readily carried out by reacting at 0° C. to 30° C. for 1 to 20 hours in a suitable non-reactive reaction medium such as methanol, ethanol, other lower alcohols, lower esters, halogenated hydrocarbons, and mixtures of these. Preferred reaction conditions are 15° C. to 25° C. for 2 to 10 hours in methanol. Triethylamine or other tertiary amine can be used to convert amine salt to the free base for reaction. 2-Pyridyldithioethylamine hydrochloride is readily formed by starting with the known disulfide $H_3COOCSSCH_2CH_2NH_2.HCl$ and reacting with 3-nitro-2-mercaptopyridine according to the procedure of Brois, S.J., et al, J. Am. Chem. Soc. 92, 7629–7631 (1970). According to EP 116208, 2-pyridyldithioethylamine dihydrochloride is disclosed in a Japanese Patent Application laid open to public inspection as Kokai Koho 136,261/80.

The process for conversion to 7-[2-(3-nitro-2-pyridyldithio)ethylamino]-9a-methoxymitosane comprises reacting 7-(diphenylmethyl)oxy-9a-methoxymitosane with 2-(3-nitro-2-pyridyldithio)ethylamine, e.g., as the hydrochloride salt. This reaction is readily carried out by reacting at 0° C. to 30° C. for 1 to 20 hours in a suitable non-reactive reaction medium such as methanol, ethanol, other lower alcohols, halogenated hydrocarbons and mixtures of these. Preferred reaction conditions are 0° to 30° C. for 2 to 10 hours in methanol. Triethylamine or other tertiary amine can be used to convert amine salt to the free base for reaction. 2-(3-Nitro-2-pyridyldithioethylamine) hydrochloride is readily formed by starting with the known disulfide $H_3COOCSSCH_2CH_2NH_2.HCl$ and reacting with 3-nitro-2-mercaptopyridine according to the procedure of Brois, S.J, et al, J. Am. Chem Soc. 92, 7629–7631 (1970). The preparation of 3-nitro-2-mercaptopyridine is described in Surrey, A.R., et al, J. Am. Chem. Soc 62, 1697–1698 (1940).

The intermediate 7-[2-(2-pyridyldithio)ethylamino-9a-methoxy-mitosane is a known compound and is described in Shirahata et al U.S. Pat. No. 4,691,024 at column 4 and in Kono et al European 116208 at page 5. It is readily reacted in a thiol exchange process with thiol reactant. Suitable thiol reactants include those named in EP 116208 and in Shirahata U.S. Pat. No. 4,691,024. Reaction is readily carried out using a greater than stoichiometric amount of thiol reactant (e.g., up to 2 equivalents or more) over a time period ranging from 2 minutes to 10 hours at 0° C. to 30° C. in an inert reaction medium such as methanol, or other solvent which is compatible with the reaction. In a very important embodiment of this reaction, 7-[2-(2-pyridiyldithio)ethylamino]-9a-methoxymitosane is reacted with p-nitrothiophenol, preferably in methanol at 0° to 30° C. for 10 to 20 minutes to produce the very effective antitumor agent 7-[2-(4-nitrophenyldithio)ethylamino]-9a-methoxymitosane.

The intermediate 7-[2-(3-nitro-2-pyridyldithio)ethylamino]-9a-methoxymitosane is a known compound and is designated Compound 30 (Procedure 30) in Vyas et al U.S. Pat. No. 4,691,023. The reaction of this intermediate in a disulfide thiol exchange process is described in Vyas et al, U.S. Ser. No. 4,866,180 and the thiols indicated therein as reacted with said intermediate are incorporated herein by reference. The reaction of this intermediate with thiols in a thiol exchange process is readily carried out at 0° to 60° C. in a time period ranging from 2 minutes to 10 hours in a non-reactive reaction medium preferably one in which the reactants are soluble. With water-soluble thiol reactants, water is suitable reaction medium. With water-insoluble thiol reactants, an organic solvent is preferred. Suitable organic reaction media include, for example, lower alkanols, such as methanol, ethanol and isopropanol, lower alkanoic lower alkyl esters such as ethyl acetate, methyl propionate, and butyl acetate, lower aliphatic ketones such as acetone and methylethylketone, cyclic aliphatic ethers such as tetrahydrofuran and lower polyhalogenated aliphatic hydrocarbons such as methylene chloride, ethylene dichloride, and chloroform. In a very important embodiment of this reaction, 7-[2-(3-nitro-2-pyridyldithio)ethylamino]-9a-methoxymitosane is reacted with p-nitrothiophenol, preferably in methanol for 2 to 20 minutes at 0° to 30° C. to produce the antitumor agent 7-[2- (4nitrophenyldithio)ethylamino)]-9 a-methoxymitosane.

The invention is illustrated in the following specific examples. In the Examples MeOH stands for methanol and EtOAc stands for ethyl acetate.

EXAMPLE I

Mitomycin C (817 mg; approximately 95% pure) (2.45 mM) was placed in a round bottom flask. To this was added 1.1 eq of a 0.1M NaOH aqueous solution. This was stirred at 35° C. for 2½ hours. The resulting blue solution was cooled to −78° C. and lyophilzed at 0.1 mm Hg vacuum. After 18 hours an essentially dry dark solid was obtained, and acetone (12.2 mL) was added to the dark solid. This was stirred as a suspension for 15 minutes prior to the addition of Dowex AGX8 strong acid cation exchange resin in the hydrogen form (3.65 g). The resulting combination was gently stirred for 1½ hours at 22° C. The material was then filtered and the resin washed with 10 mL of acetone. The filtrate was evaporated, and to the dark residue was added methylene chloride, 25 mL. Next was added a 0.7 mM diazodiphenylmethane solution in methylene chloride (6.6 mL; approximately 2 eq). After 1 hour another 6.6 mL of diazodiphenylmethane solution was added. After a total of 4 hours, TLC-SiO$_2$ 7% MeOH/CH$_2$Cl$_2$ indicated the starting material was gone and there was the presence of less polar red spot. The reaction mixture was then poured onto the top of a dry Al$_2$O$_3$ column and eluted with CH$_2$Cl$_2$, followed by a gradient to approximately 4% MeOH/CH$_2$Cl$_2$. The desired fractions were pooled and evaporated to yield 7-(diphenylmethyl)oxy-9a-methoxymitosane as a dark maroon solid, 775 mg (1.55 mM) in 66% yield. A sample of this was crystallized from a mixture of acetone/CH$_2$Cl$_2$/ether/hexane. Analysis gave the following results: $^1$H-NMR (pyr-d5), signals at δ. 1.85 (3H, s), 2.04 (1H, t), 2.68 (1H, brs); 3.08 (1H,d), 3.11 (3H, s), 3.43 (1H, d), 3.96 (1H, dd), 4.08 (1H, d), 5.02 (1H, t), 5.43 (1H, dd), 7.19 to 7.38 (10H, m) and 7.42 (1H, s); UV λmax (methanol) 206, 325, 528 nm; IR, KBr major bands 3427, 1730, 1632, 1578, 1450, 1404 and 1330 cm$^{-1}$. The product has a melting point of 96°–97° C.

EXAMPLE II

In a 3-neck round bottom flask was placed 353 mg (1.06 mM) of Mitomycin C (approximately 95% pure). To this was added 11.6 mL of 0.1N NaOH. This was stirred at 35° C. for 2 hours. The hydrolysis reaction was essentially complete at this time. After cooling to approximately 0° C., the reaction mixture was adjusted to pH of approximately 6 by the addition of 10% H$_3$PO$_4$ (aq.). To the reaction mixture was then added 3 mL (approximately 2.1 mM) of a 0.7 molar solution of diazodiphenylmethane (DDM) in methylene chloride. To this was added 3 mL of methanol followed by stirring rapidly for 1 hour. The pH was then adjusted to approximately 5 by the addition of more 10% H$_3$PO$_4$ with continued stirring. After 2 hours with periodic addition of 10% H$_3$PO$_4$ to keep the pH between 5–6, addition 3 mL of 0.7 molar diazodiphenylmethane (DDM) solution in methylene chloride was added. This was allowed to gradually warm to 22° C. After a total of 6 hours from the initial addition of DDM solution, the reaction mixture was partitioned between 100 mL of CH$_2$Cl$_2$ and 20 mL of H$_2$O. The organic phase was dried over Na$_2$SO$_4$ and evaporated. The residue was chromatographed on a dry neutral Al$_2$O$_3$ column with a gradient from CH$_2$Cl$_2$ to 4% MeOH/CH$_2$Cl$_2$ used to elute the desired compound. Pure fractions were pooled and evaporated to yield 209 mg of 7-(diphenylmethyl)oxy-9a-methoxymitosane (approximately 42% yield). The aqueous layer following the partitioning was treated with 6 mL of 0.7 molar DDM solution in CH$_2$Cl$_2$ and the combination was stirred rapidly at 22° C. After 16 hour the reaction mixture was worked up as above and then chromatographed similarly to yield an additional 49 mg (approximately 10% additional yield)

of 7-(diphenylmethyl)oxy-9a-methoxymitosane. The total yield was 52%.

EXAMPLE III

In a round bottom flask was placed 7-(diphenylmethyl)oxy-9a-methoxymitosane (100 mg) (0.2 mM). This was dissolved in 8 mL of methanol to which was then added 123 mg (5 eq). of p-anisidine. The reaction mixture gradually turned from maroon to green. The reaction was monitored by TLC on silica gel using 5% MeOH/$CH_2Cl_2$. After a total 2.75 hours, the reaction mixture was evaporated, and the residue was dissolved in $CH_2Cl_2$. This was chromatographed on a silica gel column packed and eluted with 5% MeOH/$CH_2Cl_2$. The pure green band was collected and evaporated to yield 76 mg (86%) of 7-(4-anidino)-9a-methoxymitosane. A $^1H$ NMR was consistent the product being this compound.

EXAMPLE IV

In a round bottom flask was placed 42 mg of 7-(diphenylmethyl)oxy-9a-methoxymitosane. To this was added 2 mL of methanol and 100 microliters of morpholine. The resulting combination was stirred at 23° C. for 48 hr. The reaction was essentially complete at this time. The reaction mixture was evaporated and chromatographed on a silica gel column packed and eluted with 7% MeOH/$CH_2Cl_2$ to yield 22 mg (65%) of 7-(N-morpholino)-9a-methoxymitosane. A $^1H$ NMR was consistent for the product being this compound.

EXAMPLE V 7-(Diphenylmethyl)oxy-9a-methoxymitosane (71 mg) (0.14 mM) was dissolved in methanol (6 mL). The resulting solution was stirred and to the stirred solution was added ethanolamine (100 microliters). The reaction mixture was stirred at 22° C. and reaction was monitored by TLC on $SiO_2$ using 15% MeOH/$CH_2$ $Cl_2$. After 2 hours the reaction was complete. The reaction mixture was then diluted with methylene chloride (20 mL). The resulting solution was chromatographed on a column of $SiO_2$, packed and eluted using 10% MeOH/$CH_2Cl_2$ with a gradient to 20% MeOH/$CH_2Cl_2$. The blue band was collected and evaporated to yield 7-(2-hydroxyethyl)amino-9a-methoxymitosane (45 mg) (83% yield ). A $^1H$ NMR was consistent for this compound.

EXAMPLE VI 7-(Diphenylmethyl)oxy-9a-methoxymitosane (178 mg, 0.355 mM) was placed in a round bottom flask. Next was added dry methanol (15 mL). The resulting solution was stirred and to this stirred solution was added a 1.62% KOH in methanol solution (301 microliters). The reaction was monitored by TLC $SiO_2$, 10% MeOH/$CH_2Cl_2$. After 5½ hours the reaction appeared >90% complete. The reaction was then quenched by the addition of dry ice (about 0.5 g). The reaction mixture was then evaporated and the residue chromatographed on an $SiO_2$ column eluted with a gradient from 7% MeOH/$CH_2Cl_2$ to 10% MeOH/$CH_2Cl_2$. Fractions were collected and similar ones pooled to yield mitomycin A (88 mg) (0.252 mM), 71% yield. A $^1H$ NMR was identical with an authentic sample.

EXAMPLE VII

In a round bottom flask was placed 7-(diphenylmethyl)oxy-9a-methoxymitosane (209 mg) (0.417 mM). This was dissolved in 7.3 mL of methanol and the resulting solution was cooled to 0° C., followed by the addition of 116 microliters of triethylamine (2 eq.). Next was added 122 mg of 2- (p-nitrophenyldithio)ethylamine hydrochloride. The reaction mixture was allowed to warm to 22° C. After 1½ hour, the reaction mixture was again cooled to 0° C. and 232 microliters of triethylamine was added followed by 244 mg of 2-(p-nitrophenyldithio)ethylamine hydrochloride. The reaction mixture was again allowed to warm to 22° C. After 6 hours the reaction was complete as indicated by TLC on $SiO_2$ - 10% MeOH/$CH_2Cl_2$. The reaction mixture was evaporated, and the residue was dissolved in $CH_2Cl_2$ and the resulting solution was chromatographed on an $SiO_2$ packed column and eluted with 5% MeOH/$CH_2Cl_2$ to a gradient of 10% MeOH/$CH_2Cl_2$. Fractions containing the desired blue band were collected and analyzed by TLC. Pure fractions were pooled and evaporated to yield 120 mg of 7-[2-(4-nitrophenyldithio)ethylamino]-9a-methoxymitosane in 53% yield. A $^1H$ NMR showed the material was consistent for the named compound.

EXAMPLE VIII

In a round bottom flask was placed 2.50 g of $H_3COOCSSCH_2CH_2NH_2$ hydrochloride. This was dissolved in 100 mL of methanol followed by cooling to −10° C. The resulting solution was stirred. To the stirred solution was then added dropwise 1.37 g eq.) of 2-thiopyridine in 40 mL of methanol. The resulting yellow solution was stirred at −10° C. for 1½ hours, then evaporated on a rotovapor at 20° C. The residue was triturated with ether and ethyl acetate, then evaporated again. This time a pale yellow solid was present. The solid was triturated 2×50 mL with ether and then evaporated to yield 2.49 g of a yellow solid. This was crystallized from MeOH/EtOAc to yield 2.22 g of 2-pyridyldithioethylamine hydrochloride (82% yield).

7-(Diphenylmethyl)oxy-9a-methoxymitosane (770 mg) (1.537 mM) was placed in a round bottom flask and dissolved in 6 mL of methanol. This was added to a solution of 2-pyridyldithioethylamine hydrochloride (631 mg) (2.84 mM) and 435 microliters of triethylamine (3.13 mM) (1.1 equivalents based on the hydrochloride) in 10 mL of methanol. The resulting solution was stirred at 22° C. and reaction was monitored by TLC ($SiO_2$, 7% MeOH/$CH_2Cl_2$). After 8 hours reaction was about 90% complete. The reaction mixture was then worked up by diluting with 120 mL of $CH_2Cl_2$ and then washing with 2×30 mL of $H_2O$. The organic layer was dried over $Na_2SO_4$ and evaporated, and the residue was chromatographed on $SiO_2$ using 7% MeOH/$CH_2Cl_2$. This yielded 495 mg of 7-[2-(2-pyridyldithio)ethylamino]-9a-methoxymitosane in 64% yield (0.98 mM).

The product from the synthesis in the above paragraph was placed in a round bottom flask and dissolved in 8 mL of methanol. Next was added in two portions 190 mg, (1.23 mM) 1.25 eq., of p-nitrothiophenol in 16 mL of methanol. The resulting solution was stirred for 15 minutes at which time the reaction was indicated to be >95% complete. The reaction mixture was diluted with 120 ml $CH_2Cl_2$, then washed with 1×30 mL $H_2O$, 2×30 mL brine, dried over $Na_2SO_4$, evaporated and chromatographed on $SiO_2$ using 7% MeOH/$CH_2Cl_2$ to elute. This yielded 480 mg of pure 7-[2-(4-nitrophenyldithio)ethylamino]-9a-methoxymitosane, sometimes denoted BMY 25067 hereinafter (0.91 mM), 88% yield.

The yield of BMY 25067 from 7-(diphenylmethyl)oxy-9a-methoxy-mitosane was about 56% and from Mitomycin C was about 31%.

The yield of BMY 25067 from an 880 mg sample of 7-(diphenyl-methyl)oxy-9a-methoxymitosane proceeding in one step as in Example VII was about 23% based on Mitomycin C.

EXAMPLE IX

7-Hydroxy-9a-methoxymitosane was alkylated with 3-methyl-1-p-tolyltriazene to give mitomycin A or with diazodiphenylmethane to give 7-(diphenylmethyl)oxy-9a-methoxymitosane (hereinafter 7-ODPM mitomycin).

Each of the intermediates, mitomycin A and 7-ODPM mitomycin, were evaluated for conversion to 7-[2-(4-nitrophenyldithio)ethylamino]-9a-methoxymitosane, BMY-25067, by a one-step process where the intermediates were reacted with 2-(p-nitrophenyldithio)ethylamine hydrochloride, Routes A and D respectively; and in a two-step process where in the first step the intermediates were converted to 7-[2-(2-pyridyldithio)ethylamino]-9a-methoxymitosane which in turn in the second step was converted to BMY-25067, Routes B and E respectively; and in a two-step process where in the first step the intermediates were converted to 7-[2-(3-nitro-2-pyridyldithio)ethylamino]-9a-methoxymitosane which in turn in the second step was converted to BMY-25067, Routes C and F respectively. Results are presented in the following Table I wherein "POT stands for potency.

TABLE I

| STARTING MATERIAL | ROUTE | INPUT WEIGHT | INTERMEDIATE YIELD | BMY-25067 YIELD | OVERALL YIELD | POTENCY | ACTIVITY YIELD |
| --- | --- | --- | --- | --- | --- | --- | --- |
| MITOMYCIN A | A | 3.15 | — | 57.6 | 57.6 | 88.4 | 62.3[a] |
| POT: 81.7% | B | 4.02 | 82 | 43.7 | 35.8 | 82 | 35.9 |
|  | C | 4.02 | 100 | 84.9 | 84.9 | 85.9 | 89.3 |
| 7-ODPM | D | 3.51 | — | 36.3 | 36.3 | 78.7 | 29.0 |
| MITOMYCIN | E | 3.70 | 61.7 | 72.8 | 44.9 | 87 | 39.6 |
| POT: 98.6% | F | 3.70 | 97.0 | 82.7 | 80.2 | 85.8 | 69.8 |

[a]This yield was occasionally obtained. Yields are typically lower (40%)

EXAMPLE X 7-(Diphenylmethyl)oxy-9a-methoxymitosane (171 mg, 0.355 mM) was added to a saturated solution of $NH_3$ in methanol at 20° C. The resulting solution was stirred for 16 hours at 20° C. The solvent was then evaporated. The residue was flash chromatographed on a $SiO_2$ column packed and eluted with 10% methanol/$(CH_2Cl_2)$. A gradient was run to 15% methanol/$CH_2Cl_2$. Fractions were analyzed by thin layer chromatography and similar pure ones were pooled and evaporated to yield mitomycin C, 101 mg (85% yield). A $^1H$ NMR of the material was identical to an authentic sample.

EXAMPLE XI $CDF_1$ female mice implanted intraperitoneally with a tumor inoculum of $10^6$ ascites cells of P-388 murine leukemia were treated with doses as stated hereinafter with 7-(diphenylmethyl)oxy-9a-methoxymitosane. The treatment compound was administered by intraperitoneal injection. Groups of four mice were used for each dosage amount and each mouse was treated with a single dose of the treatment compound on the day of inoculation. A group of ten saline treated control mice was included. The mice were weighed before treatment and again on day six. The change in weight was taken as a measure of drug toxicity. Mice weighing 20 grams each were employed and a loss in weight of up to approximately 2 grams was not considered excessive. Results are given in mean survival time (MED S.T.), % T/C (ratio of mean survival time of test compound treated group to the mean survival time of the saline treated control group), average weight change as of day six (AWC) and number of mice alive on day five/total mice treated (A/T). The saline treated mice usually died within 9 days. A minimum effect in terms of % T/C was considered to be 125.

| Dose (mg/kg) | MED. S.T. | % T/C | AWC | A/T |
| --- | --- | --- | --- | --- |
| 300 | TOXIC | TOXIC | −0.7 | 2/4 |
| 150 | 13.5 | 150 | 0.0 | 4/4 |

The above results indicate antitumor inhibition effect at a dosage of 150 mg/kg.

In view of the antitumor activity observed in experimental animals, the invention includes use of the novel compound of the present invention for inhibiting mammalian tumors. For this purpose, it is administered systemically to a mammal bearing a tumor in a substantially nontoxic antitumor effective dose. The compound is intended primarily for use by injection in much the same way and for some of the same purposes as mitomycin C. Somewhat larger or smaller doses may be employed depending on the particular tumor sensitivity. The novel compound herein is readily distributed as dry pharmaceutical compositions containing diluents, buffers, stabilizers, solubilizers and ingredients contributing to pharmaceutical elegance. These compositions are constituted with an injectable liquid medium extemporaneously just prior to use. Suitable injectable liquids include water, isotonic saline and the like.

Variations will be obvious to those skilled in the art. Thus, the invention is to be defined by the claims.

What is claimed is:

1. Process for the preparation of 7-(diphenylmethyl)oxy-9a-methoxymitosane comprising the step of reacting 7-hydroxy-9a-methoxymitosane with diazodiphenylmethane to produce 7-(diphenylmethyl)oxy-9a-methoxymitosane.

2. The process of claim 1 wherein said step is carried out utilizing a reaction solvent comprising methylene chloride.

3. The process of claim 1 wherein said step is carried out in the presence of water.

4. The process of claim 3 wherein said step is carried out utilizing as a reaction solvent methylene chloride and methanol in a volume ratio of methylene chloride to methanol ranging from 0.5:1 to 3:1, a reaction temperature ranging from 0° to 30° C. and a pH ranging from about 4.7 to 6.5.

5. The process of claim 4 wherein said pH ranges from about 5 to about 6.

6. Process for the preparation of 7-(diphenylmethyl)oxy-9a-methoxymitosane, said process comprising the steps of
   (a) reacting mitomycin C with aqueous hydroxide solution to produce an aqueous solution of basic 7-salt oxide-9a-methoxymitosane,
   (b) admixing the aqueous solution of basic 7-salt oxide-9a-methoxymitosane with acid and diazodiphenylmethane and solvent in which 7-hydroxy-9a-methoxymitosane and diazodiphenylmethane have at least some solubility and reacting to form 7-(diphenylmethyl)oxy-9a-methoxymitosane.

7. The process of claim 6 wherein the aqueous hydroxide solution in step (a) is aqueous sodium hydroxide solution, wherein the acid in step (b) is phosphoric acid and wherein step (b) is carried out at a temperature ranging from 0° C. to 30° C. in a reaction solvent combination of methylene chloride and methanol in a volume ratio of methylene chloride to methanol ranging from 0.5:1 to 3:1.

8. Process for the preparation of 7-(diphenylmethyl)oxy-9a-methoxymitosane, said process comprising the steps of:
   (a) reacting 7-salt oxide-9a-methoxymitosane with strong acid cation exchange resin in the hydrogen form in sufficient amount to convert 7-salt oxide group to 7-hydroxy group to thereby form 7-hydroxy-9a-methoxymitosane,
   (b) reacting 7-hydroxy-9a-methoxymitosane with diazodiphenylmethane to form 7-(diphenylmethyl)-oxy-9a-methoxymitosane.

* * * * *